United States Patent
Stypulkowski

(10) Patent No.: US 6,909,918 B2
(45) Date of Patent: Jun. 21, 2005

(54) IMPLANTABLE PERCUTANEOUS STIMULATION LEAD WITH LEAD CARRIER

(75) Inventor: Paul Stypulkowski, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 481 days.

(21) Appl. No.: 09/975,622

(22) Filed: Oct. 10, 2001

(65) Prior Publication Data

US 2003/0069623 A1 Apr. 10, 2003

(51) Int. Cl.[7] .............................................. A61N 1/05
(52) U.S. Cl. ..................................................... 607/117
(58) Field of Search ...................... 607/116–118, 4.5, 607/123, 122–128; 600/393, 373–381; 24/570; 439/909, 668

(56) References Cited

U.S. PATENT DOCUMENTS

| RE26,810 E | * | 3/1970 | Schwartz et al. ............ 607/118 |
|---|---|---|---|
| 4,601,713 A | | 7/1986 | Fuqua |
| 4,744,371 A | * | 5/1988 | Harris ......................... 607/117 |
| 5,107,856 A | | 4/1992 | Kristiansen et al. |
| 5,265,608 A | * | 11/1993 | Lee et al. .................... 600/377 |
| 5,354,326 A | * | 10/1994 | Comben et al. ............. 607/115 |
| 5,458,629 A | * | 10/1995 | Baudino et al. ............. 607/116 |
| 5,578,067 A | * | 11/1996 | Ekwall et al. ............... 607/122 |
| 5,676,694 A | * | 10/1997 | Boser et al. ................. 607/122 |
| 5,702,270 A | * | 12/1997 | Casica et al. ................ 439/528 |
| 5,895,416 A | * | 4/1999 | Barreras et al. .............. 607/62 |
| 5,899,933 A | * | 5/1999 | Bhadra et al. ................ 607/118 |
| 5,935,159 A | * | 8/1999 | Cross et al. ................. 607/116 |
| 5,938,596 A | * | 8/1999 | Woloszko et al. ........... 600/377 |
| 5,957,968 A | * | 9/1999 | Belden et al. ............... 607/126 |
| 5,964,793 A | * | 10/1999 | Rutten et al. ................ 607/119 |
| 6,078,839 A | * | 6/2000 | Carson ........................ 607/116 |
| 6,205,361 B1 | | 3/2001 | Kuzma et al. |
| 6,212,434 B1 | * | 4/2001 | Scheiner et al. ............. 607/123 |
| 6,216,045 B1 | * | 4/2001 | Black et al. ................. 607/122 |

OTHER PUBLICATIONS

MEDTRONIC, "Implant Manual Pisces Quad®" Medtronic,Inc. Brochure (1996).

* cited by examiner

Primary Examiner—Jeffrey R. Jastrzab
(74) Attorney, Agent, or Firm—Shumaker & Sieffert, P.A.

(57) ABSTRACT

An implantable neurological stimulation lead has a lead carrier with an attachment detail for coupling to a first lead body first distal end and an electrode shield to insulate a portion of the electrode. The first lead body has an outer body, a first distal end, and a first proximal end. The first lead body includes at least one electrode carried on the first distal end, at least one electrical connector carried on the first proximal end, and at least one conductor electrically connecting the electrode to the electrical connector and insulated by the lead body. The lead carrier has many embodiments and methods of operation.

17 Claims, 5 Drawing Sheets

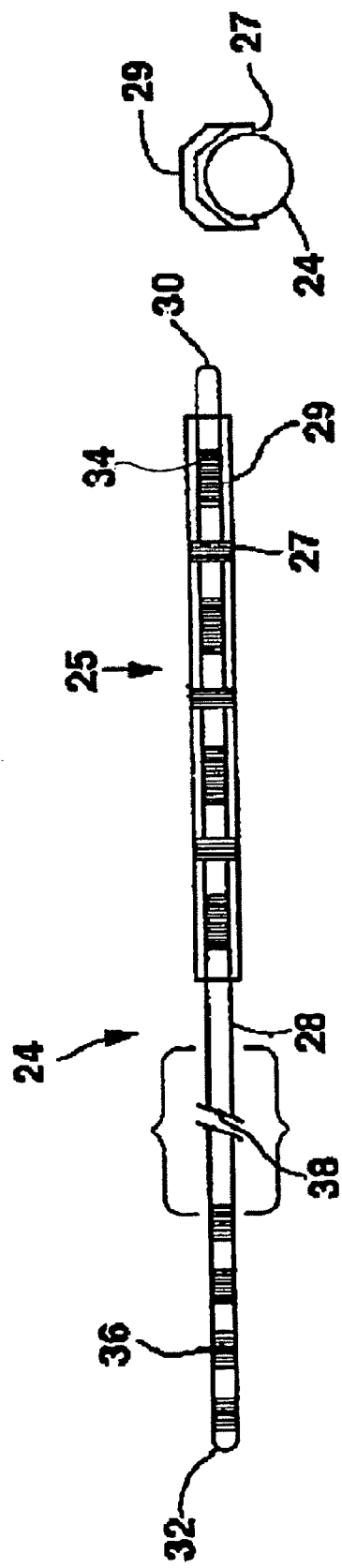
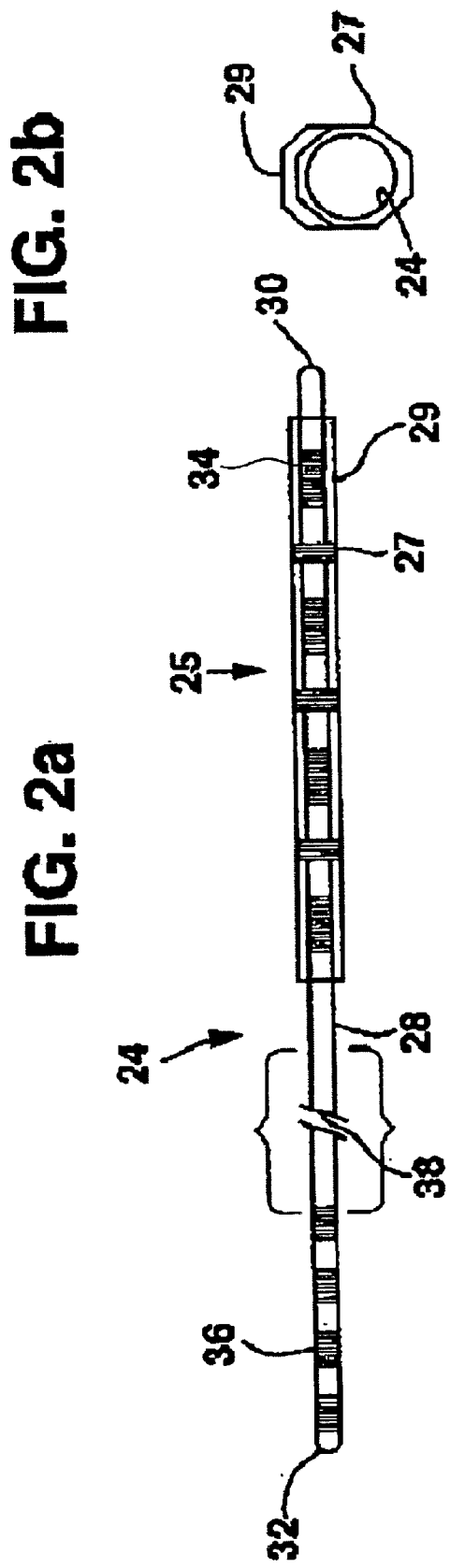

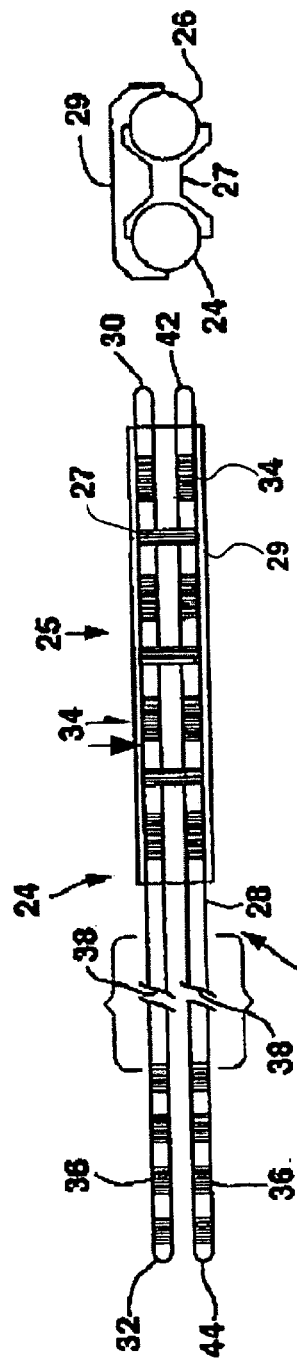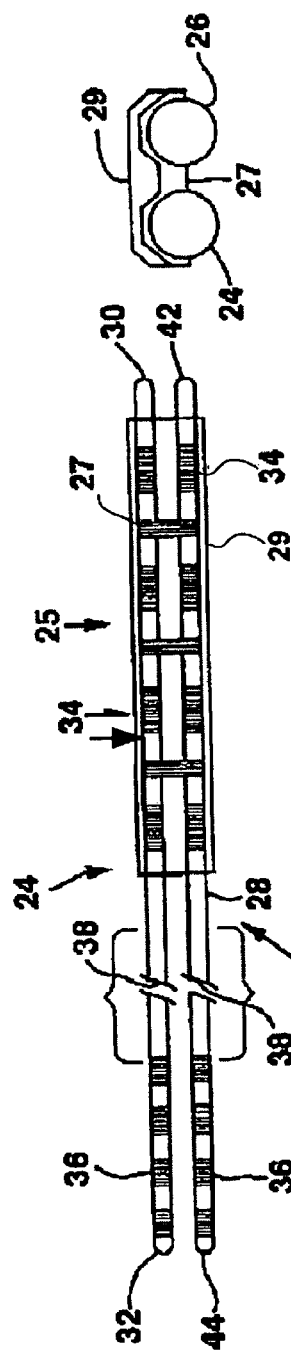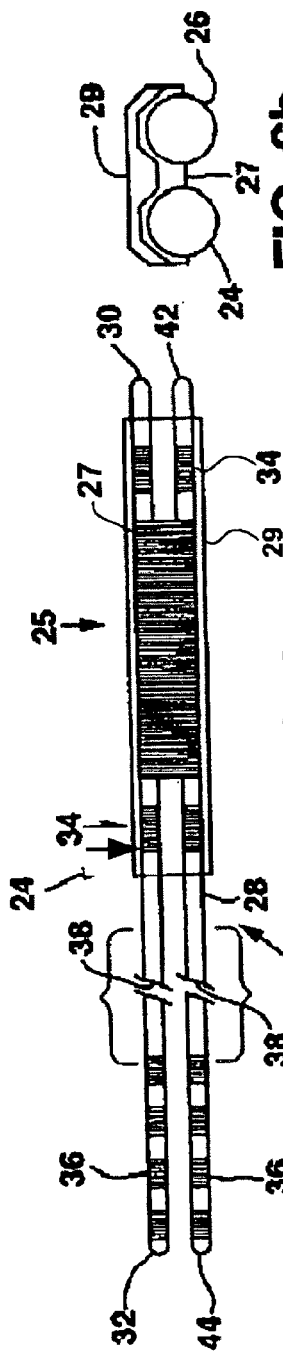

IMPLANTABLE PERCUTANEOUS STIMULATION LEAD WITH LEAD CARRIER

CROSS-REFERENCE

This disclosure is related to the following co-pending applications entitled "Implantable Percutaneous Stimulation Lead With Interlocking Elements" by inventors Vinup et al., filed on Sep. 20, 2001, "Surgical Lead Body" by inventor Cross, Ser. No. 09/500,201 filed Feb. 8, 2000, "Apparatus And Method For Percutaneous Implant Of A Paddle Style Lead" by Redko et al., Ser. No. 09/302,694 filed Apr. 30, 1999, which are not admitted as prior art with respect to the present disclosure by its mention in this section.

FIELD OF THE INVENTION

This invention relates to a medical device and more particularly to a neurological stimulation lead that can be implanted in a human body.

BACKGROUND OF THE INVENTION

The medical device industry produces a wide variety of electronic and mechanical devices such as neurological stimulators, therapeutic substance infusion pumps, pacemakers, and defibrillators for treating patient medical conditions such as pain, movement disorders, functional disorders, spasticity, cancer, and cardiac disorders. Medical devices can be configured to be surgically implanted or connected externally to the patient receiving treatment and can be used either alone or in combination with pharmaceutical therapies and surgery to treat patient medical conditions. For certain medical conditions, medical devices provide the best and sometimes the only therapy to restore an individual to a more healthful condition and a fuller life. One type of medical device is an implantable neurological stimulation system which typically includes a neurostimulator, an electrical stimulation lead, and an extension such as shown in Medtronic, Inc. brochure "Implantable Neurostimulation System" (1998). An implantable neurological stimulation system delivers electrical pulses to tissue such as neurological tissue or muscle to treat a medical condition.

One application of neurological stimulation systems is for spinal cord stimulation (SCS) to treat chronic pain. In many cases, the leads used for SCS are implanted percutaneously, through a large needle inserted into the epidural space. When a percutaneous lead is used for SCS, there can be undesirable current flow into areas of the patient's anatomy away from the spinal cord, because the electrodes typically cover the circumference of the stimulation lead. Additionally, dual percutaneous lead implants are becoming more common in the clinical practice of SCS. Currently, most dual lead systems are implanted as two individual single lead implants (i.e., two separate needle sticks, two separate lead insertions). Implanting dual leads in this way makes it difficult to control the relative position of the two leads with respect to one another. Currently, the physician typically uses fluoroscopy to determine the relative position of the two leads, and must try to assure that the leads do not touch (leading to a potential short between electrodes) and also that the leads are not too far apart (resulting in less than optimal stimulation). To prevent shorting, one approach has been to stagger the electrode contacts, rather than placing them adjacent on the parallel leads. In addition to being difficult to position at the time of implant, once the leads are permanently implanted, there is no guarantee that the leads will not move relative to one another (i.e., migrate) potentially reducing therapy efficacy.

For the foregoing reasons, what is needed is an electrode shield that can be attached to a stimulation lead to limit current flow to a selected area around the electrode, and a means for coupling more that one lead together in a controlled fashion.

BRIEF SUMMARY OF THE INVENTION

An implantable neurological stimulation lead with lead carrier has a lead carrier with an attachment detail for coupling to a first lead body first distal end and an electrode shield to insulate a portion of the electrode. The first lead body has an outer body, a first distal end, and a first proximal end. The first lead body includes at least one electrode carried on the first distal end, at least one electrical connector carried on the first proximal end, and at least one conductor electrically connecting the electrode to the electrical connector and insulated by the lead body. The implantable neurological stimulation lead with lead carrier has many embodiments and methods of operation.

BRIEF DESCRIPTION OF THE DRAWINGS

FIG. 2a shows a lead carrier configured for a single stimulation lead having a single lead clip embodiment;

FIG. 2b shows a cross-section of FIG. 2a;

FIG. 3a shows a lead carrier configured for a single stimulation lead having a single lead ring embodiment;

FIG. 3b shows a cross-section of FIG. 3a;

FIG. 4a shows a lead carrier configured for two stimulation leads having a dual medical clip embodiment;

FIG. 4b shows a cross-section of FIG. 4a;

FIG. 5a shows a lead carrier configured for two stimulation leads having a dual lead clip embodiment;

FIG. 5b shows a cross-section of FIG. 5a;

FIG. 6a shows a lead carrier configured for two stimulation leads having a dual lead sleeve embodiment;

FIG. 6b shows a cross-section of FIG. 6a;

DETAILED DESCRIPTION OF THE INVENTION

Figure 1:
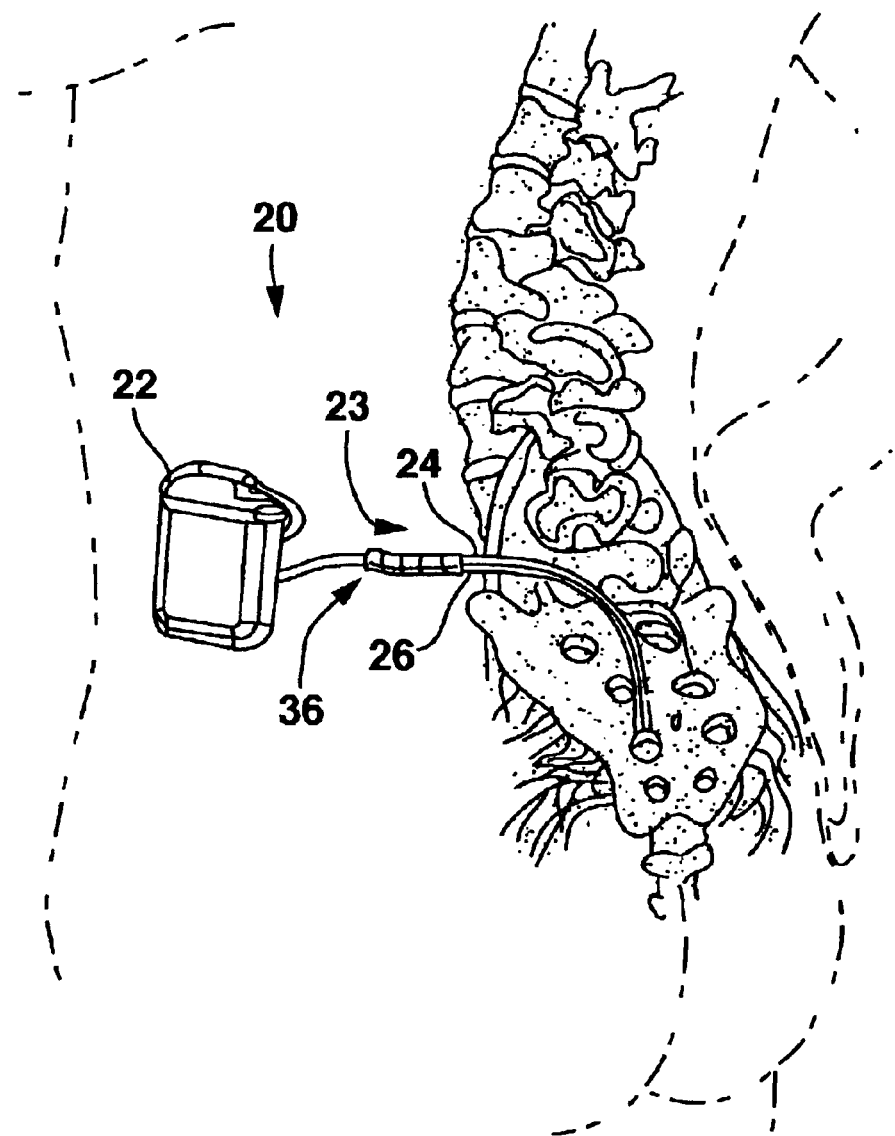
FIG. 1 shows a neurological stimulation system environment embodiment.

FIG. 1 shows an environment of an implantable neurological stimulation system 20. The implantable neurological stimulation system 20 comprises an implantable neurological stimulator 22, a stimulation lead with lead carrier 23, a first lead body 24, and a second lead body 26. The implantable neurological stimulator 22 provides a programmable stimulation signal that is delivered to a desired location or target to stimulate selected nerves or muscle tissue. The implantable neurological stimulator 22 is typically implanted in a subcutaneous pocket around the upper buttocks sometime after the stimulation lead has been implanted and its effectiveness verified. The implantable percutaneous stimulation lead with lead carrier would be particularly relevant for spinal cord stimulation therapies to treat pain. For a spinal cord therapy the implantable percutaneous stimulation lead with lead carrier would typically be inserted into the epidural space through a large gauge epidural needle.

FIG. 2a shows a lead carrier configured for a single stimulation lead having a single lead clip embodiment, and FIG. 2b shows a cross-section of FIG. 2a. FIG. 3a shows a lead carrier configured for a single stimulation lead having a single lead ring embodiment, and FIG. 3b shows a cross-section of FIG. 3a. The implantable neurological stimulation lead with lead carrier comprises a first lead body 24 and a lead carrier 25. The first lead body 24 has an outer body 28, a first distal end 30, and a first proximal end 32, at least one electrode 34, at least one electrical connector 36, and at least one conductor 38. The outer body 28 is manufactured from a material that is biocompatible and electrically insulating. The electrode 34 is carried on the first distal end 30. The electrode 34 can be configured as a ring or any portion of a ring to include a substantially flat electrode. The electrical connector 36 is carried on the first proximal end 32. The conductor 38 electrically connects the electrode 34 to the connector 36 and is insulated by the outer body 28.

The lead carrier 25 has an attachment detail 27 for coupling to the lead distal end and an electrode shield 29 to insulate a portion of the electrode. The attachment detail 27 can be a wide variety of geometries that are capable of fastening to a stimulation lead 23 such as a clip, a ring, a sleeve, and the like. The attachment detail 27 would typically be positioned either medially or dorsally on the first lead body 24. In some embodiments, more than one attachment detail 27 can be used along the first lead body 24 to position the electrode shield 29.

The electrode shield 29 would typically be configured to cover the dorsal, medial, or lateral sides, or portions thereof, of the electrodes 34. When configured to cover the dorsal side of the electrodes 34, the electrode shield 29 embodiment could minimize or prevent the flow of electrical current toward dorsal ligament structures in the spine that are believed to cause pain and limit the useful stimulation signal magnitude. When configured to cover the lateral side of the electrodes 34, the electrode shield 29 embodiment could minimize or prevent the flow of electrical current laterally toward the dorsal roots. The electrode shield 29 can be manufactured from a wide range of biocompatible insulators such as a polymer and the like.

FIG. 4a shows a lead carrier configured for two stimulation leads having a dual medial clip embodiment, and FIG. 4b shows a cross-section of FIG. 4a. FIG. 5a shows a lead carrier configured for two stimulation leads having a dual dorsal clip embodiment, and FIG. 5b shows a cross-section of FIG. 5a. FIG. 6a shows a lead carrier configured for two stimulation leads having a dual lead sleeve embodiment, and FIG. 6b shows a cross-section of FIG. 6a. The second lead body 26 has a outer body 28, a second distal end 42, and a second proximal end 44, at least one electrode 34, at least one electrical connector 36, and at least one conductor 38. The outer body 28 is manufactured from a material that is biocompatible and electrically insulating. The electrode 34 is carried on the second distal end 42. The electrode 34 can be configured as a ring or any portion of a ring to include a substantially flat electrode 34. The electrical connector 36 is carried on the second proximal end 44. The conductor 38 electrically connects the electrode 34 to the connector 36 and is insulated by the outer body 28. In addition to the first lead body 24 and the second lead body 26, there can be a third lead body, a forth lead body and so on.

The lead carrier 24 when configured for more than one stimulation lead would typically use more than one attachment detail 27. The attachment details 27 can be configured to provide for desired spacing between first lead body 24 electrodes 34 and second lead body 26 electrodes 34 such as in the range from about 0.5 mm (0.0197 inches) to about 2.5 mm (0.0985 inches). A clinician could use various attachment details 27 to configure lead body spacing according to the clinician's preference or according to the patient's anatomy.

Figure 7A:
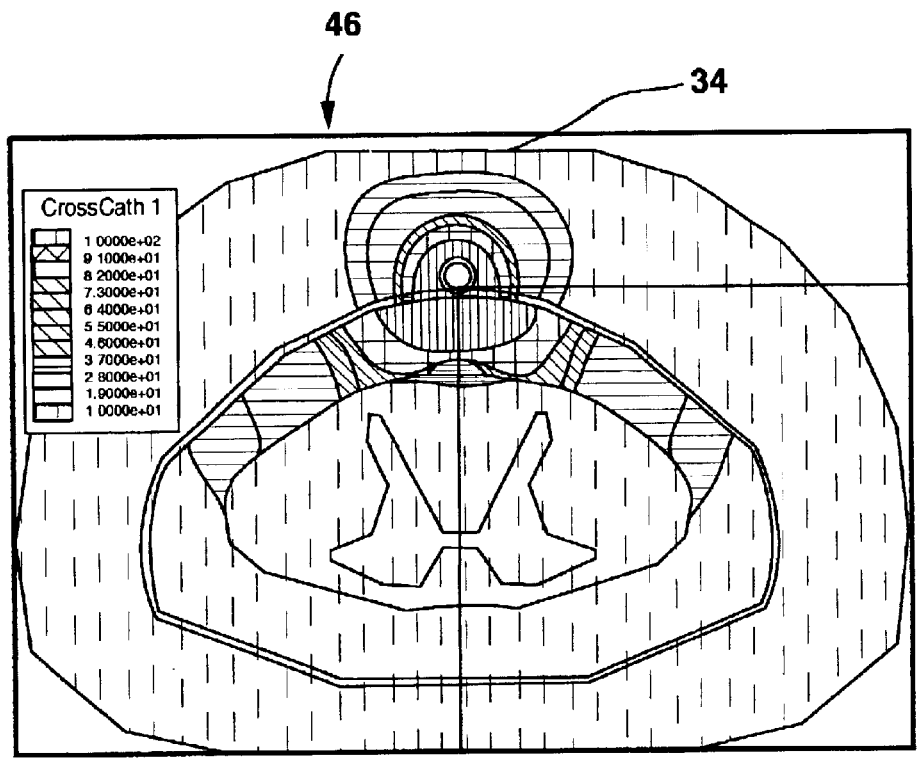
FIG. 7a (prior art) shows a example of an electrical field of a percutaneous stimulation lead.
Figure 7B:
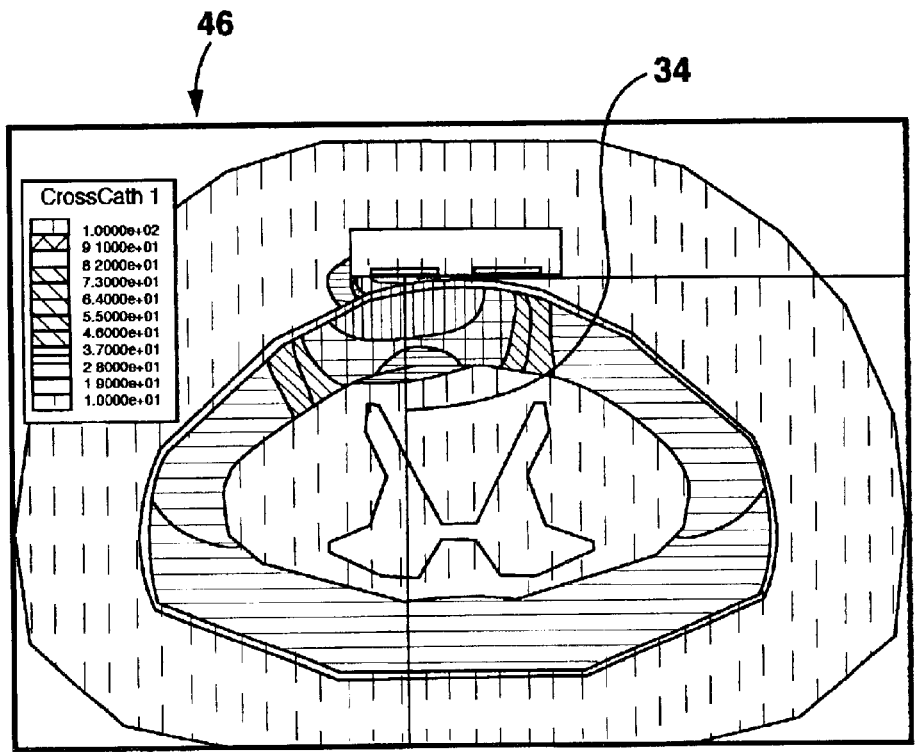
FIG. 7b shows a prophetic example of an electrical field of a percutaneous lead with a lead carrier embodiment; and, FIG. 8 shows a flow chart of a method for attaching a lead carrier to a neurological stimulation lead embodiment.

FIG. 7a (prior art) shows an example of an electrical field of a percutaneous stimulation lead, and FIG. 7b shows a prophetic example of an electrical field of a percutaneous lead with a lead carrier embodiment. In FIG. 7a, the electrical field 46 surrounding a ring electrode 34 on a neurological stimulation lead is relatively symmetric. FIG. 7b shows how the electrical field 46 surrounding an electrode 34 is believed to be influenced by the electrode shield 29. It is believed that the electrical field 46 in FIG. 7b is similar to the electrical field 46 that can be found in a surgical paddle lead such as a Medtronic Specify lead.

Figure 8:
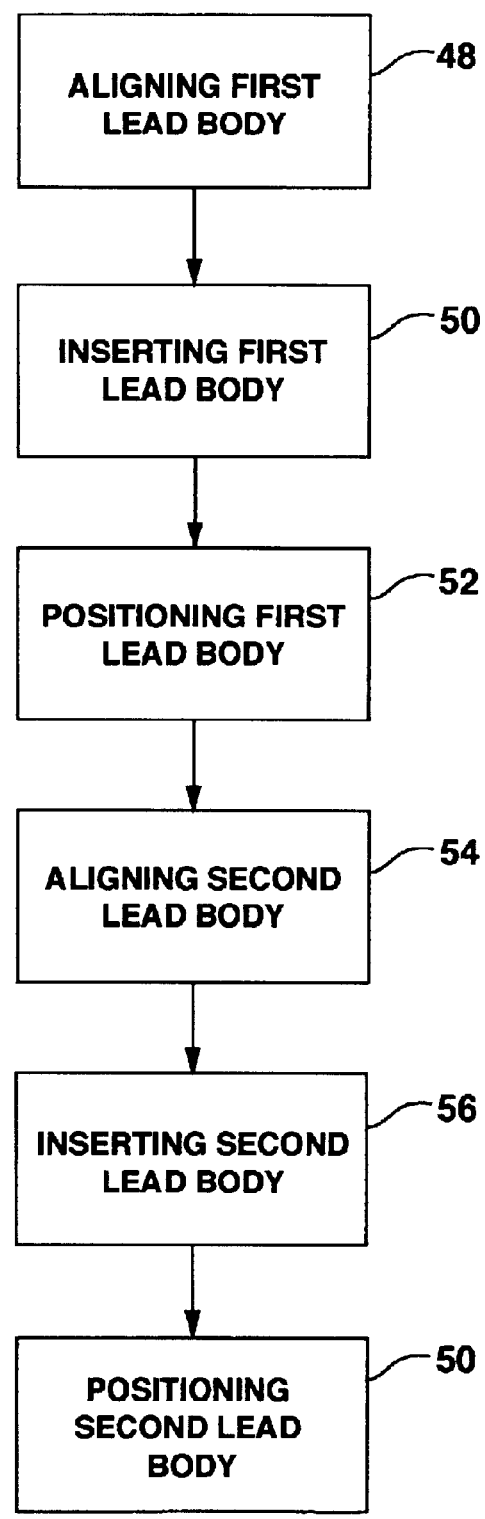

FIG. 8 shows a method embodiment for attaching a lead carrier 25 to a neurological stimulation lead. The method comprises aligning 48 a first lead body 24 in a lead carrier 25. The first lead body 24 is then inserted 50 in an attachment detail 27 of the lead carrier 25 and securely fixed to the lead carrier 25. The first lead body 24 electrode 34 is then positioned 52 in relation to the electrode shield 29 to obtain the desired shielding of the electrode 34 by the insulative electrode shield 29. A second lead body 26 is aligned 54 in the lead carrier 25. The second lead body 26 is inserted 56 in an attachment detail 27 of the lead carrier 25. The second lead body 26 electrode 34 is positioned 58 in relation to the electrode shield 29 to obtain the desired shielding of the electrode 34 by the insulative electrode shield 29. In some embodiments the first lead body 24 electrode 34 is then positioned in relation to the second lead body 26 electrode 34.

Thus, embodiments of the implantable neurological stimulation lead with lead carrier 23 are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. An implantable neurological stimulation lead comprising:
   a first lead body having g a outer body, a first distal end, and a first proximal end, the first lead body including;
   at least one ring electrode carried on the first distal end,
   at least one electrical connector carried on the first proximal end,
   at least one conductor electrically connecting the at least one ring electrode to the at least one electrical connector and insulated by the lead body; and
   a lead carrier having an attachment detail for coupling to the lead distal end and an electrode shield positioned by the attachment detail to insulate a portion of the ring electrode.

2. The implantable neurological stimulation lead as in claim 1 further comprising:
   a second lead body having a outer body, a second distal end, and a second proximal end, the second lead body including;
   at least one ring electrode carried on the second distal end,
   at least one electrical connector carried on the second proximal end, and at least one conductor electrically connecting the at least one ring electrode to the at least one electrical connector and insulated by the lead body, wherein the second lead body is configured for coupling to the attachment detail of the lead carrier to space the second lead body in relation to the first lead body.

3. The implantable neurological stimulation lead as in claim 1 wherein the attachment detail is selected from the group consisting of a clip, a ring and a sleeve.

4. The implantable neurological stimulation lead as in claim 1 wherein the attachment detail includes more than one attachment detail.

5. The implantable neurological stimulation lead as in claim 1 wherein the electrode shield is manufactured from an insulator.

6. An implantable neurological stimulation lead with a lead carrier, comprising:
a first lead body having a outer body, a first distal end, and a first proximal end, the first lead body including,
at least one ring electrode carried on the first distal end,
at least one electrical connector carried on the first proximal end,
at least one conductor electrically connecting the at least one ring electrode to the at least one electrical connector and insulated by the lead body;
a means for coupling to the lead distal end and positioning an electrode shield to insulate a portion of the ring electrode.

7. A method for attaching a lead carrier to a neurological stimulation lead, comprising:
aligning a first lead body in a lead carrier, wherein the first lead body includes a first ring electrode;
inserting the first lead body in an attachment detail of the lead carrier;
positioning the first ring electrode in relation to an electrode shield positioned by the attachment detail;
aligning a second lead body in the lead carrier, wherein the second lead body includes a second ring electrode;
inserting the second lead body in the attachment detail of the lead carrier; and,
positioning the second ring electrode in relation to the electrode shield.

8. The method as in claim 7 further comprising positioning the first ring electrode in relation to the second lead body electrode.

9. An implantable neurological stimulation lead comprising:
a lead body;
a ring electrode disposed at a distal end of the lead body;
an electrical connector disposed at a proximate end of the lead body;
a conductor electrically connecting the ring electrode to the electrical connector;
an electrically insulative shield sized to extend over a portion of the ring electrode; and
an attachment mechanism to attach the shield to the lead body, the shield at least partially insulating the portion of the ring electrode from tissue at an implantation site on a side of the shield opposite the ring electrode.

10. The lead of claim 9, wherein the attachment mechanism includes a clip, a ring or a sleeve.

11. The lead of claim 9, wherein the shield is sized to extend over less than or equal to approximately one-half of a circumference of the ring electrode.

12. An implantable neurological stimulation lead assembly comprising:
a first lead body having a first ring electrode at a distal end of the first lead body, a first electrical connector disposed at a proximate end of the first lead body, and a first conductor electrically connecting the first ring electrode to the first electrical connector;
a second lead body having a second ring electrode at a distal end of the second lead body, a second electrical connector disposed at a proximate end of the second lead body, and a second conductor electrically connecting the second ring electrode to the second electrical connector;
an electrically insulative shield sized to extend over portions of the first and second ring electrode; and
an attachment mechanism to attach the shield to the first and second lead bodies, the shield at least partially insulating the portions of the first and second ring electrodes from body tissue at an implantation site on a side of the shield opposite the first and second ring electrodes.

13. The lead assembly of claim 12, wherein the attachment mechanism includes a clip, a ring or a sleeve.

14. The lead assembly of claim 12, wherein the attachment mechanism includes a first attachment mechanism for the first lead body and a second attachment mechanism for the second lead body.

15. The lead assembly of claim 14, wherein the first and second attachment mechanisms are integrally formed with one another.

16. The lead assembly of claim 14, wherein the first and second attachment mechanisms are structured to define a degree of separation between the first and second lead bodies.

17. The lead assembly of claim 12, wherein the shield is sized to extend over less than or equal to approximately one-half of a circumference of each of the first and second ring electrodes.

* * * * *

UNITED STATES PATENT AND TRADEMARK OFFICE
CERTIFICATE OF CORRECTION

PATENT NO. : 6,909,918 B2
APPLICATION NO. : 09/975622
DATED : June 21, 2005
INVENTOR(S) : Stypulkowski Page 1 of 1

It is certified that error appears in the above-identified patent and that said Letters Patent is hereby corrected as shown below:

Col. 4, Line 47: "having g a outer" should read --having an outer--

Signed and Sealed this

Twenty-second Day of July, 2008

JON W. DUDAS
*Director of the United States Patent and Trademark Office*